(12) United States Patent
Greene

(10) Patent No.: US 9,270,137 B2
(45) Date of Patent: Feb. 23, 2016

(54) SYSTEM AND METHOD FOR CONTROLLING CHARGING ENERGY DELIVERED TO AN IMPLANTABLE MEDICAL DEVICE

(71) Applicant: Advanced Neuromodulation Systems, Inc., Plano, TX (US)

(72) Inventor: John C. Greene, Prosper, TX (US)

(73) Assignee: ADVANCED NEUROMODULATION SYSTEMS, INC., Plano, TX (US)

(*) Notice: Subject to any disclaimer, the term of this patent is extended or adjusted under 35 U.S.C. 154(b) by 155 days.

(21) Appl. No.: 14/175,642

(22) Filed: Feb. 7, 2014

(65) Prior Publication Data

US 2015/0229139 A1 Aug. 13, 2015

(51) Int. Cl.
*H02J 7/00* (2006.01)
*H02J 7/02* (2006.01)
*A61N 1/378* (2006.01)
*A61N 1/36* (2006.01)
*H02J 5/00* (2006.01)

(52) U.S. Cl.
CPC .............. *H02J 7/008* (2013.01); *A61N 1/36125* (2013.01); *A61N 1/3787* (2013.01); *H02J 7/0047* (2013.01); *H02J 7/025* (2013.01); *H02J 5/005* (2013.01); *H02J 7/0077* (2013.01); *H02J 2007/005* (2013.01)

(58) Field of Classification Search
CPC ......... H02J 7/008; H02J 7/0047; H02J 7/025; H02J 2007/005
USPC ......................................................... 320/107
See application file for complete search history.

(56) References Cited

U.S. PATENT DOCUMENTS

| | | | | |
|---|---|---|---|---|
| 5,411,537 | A * | 5/1995 | Munshi | A61N 1/3787 320/163 |
| 5,702,431 | A * | 12/1997 | Wang | A61N 1/3787 607/33 |
| 6,909,915 | B2 * | 6/2005 | Greatbatch | A61N 1/08 320/103 |
| 7,020,519 | B2 * | 3/2006 | Greatbatch | A61N 1/08 320/103 |
| 7,079,893 | B2 * | 7/2006 | Greatbatch | A61N 1/08 320/103 |
| 8,332,040 | B1 | 12/2012 | Winstrom | |
| 8,583,262 | B2 * | 11/2013 | Parramon | A61N 1/0551 607/148 |
| 8,738,155 | B2 * | 5/2014 | Zhu | A61N 1/0553 607/117 |
| 2013/0238048 | A1 * | 9/2013 | Almendinger | A61N 1/0509 607/40 |
| 2014/0070773 | A1 * | 3/2014 | Cottrill | H02J 7/0052 320/150 |
| 2014/0074185 | A1 * | 3/2014 | Fell | A61N 1/3787 607/61 |
| 2014/0266101 | A1 * | 9/2014 | Weerakoon | G05F 1/575 323/273 |

* cited by examiner

Primary Examiner — Sun Lin

(57) ABSTRACT

A charging energy control system includes an implantable medical device (IMD) and an external charger. The IMD receives charging energy to recharge a battery during a charging energy acceptance period and rejects the charging energy during an actual charging energy rejection period. The external charger transmits the charging energy to the IMD in order to recharge the battery. The external charger includes a charging controller configured to determine the actual charging energy rejection period, and regulate the charging energy during which the charging controller predicts a predicted charging energy rejection period of the IMD based on the actual recharging energy rejection period. The charging controller is configured to cease or reduce transmission of the charging energy during a charging energy conservation period that is at least a portion of the predicted charging energy rejection period.

20 Claims, 10 Drawing Sheets

SYSTEM AND METHOD FOR CONTROLLING CHARGING ENERGY DELIVERED TO AN IMPLANTABLE MEDICAL DEVICE

BACKGROUND OF THE DISCLOSURE

Embodiments of the present disclosure generally relate to implantable medical devices, and more particularly to a system and method for controlling charging energy delivered to an implantable medical device.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RE") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue (collectively hereafter "tissue") for diagnostic or therapeutic purposes.

In order to provide consistent therapy and reliable operation, IMDs are often charged and re-charged to store energy within one or more batteries. Because the IMDs are implanted within patients, the IMDs are charged by an external charger that transmits energy into the IMDs, such as through radio frequency (RF) signals.

Each IMD is generally charged as quickly and safely as possible. However, if charging energy is input into the IMD too quickly, the temperature of the IMD may increase to dangerous levels and may cause tissue damage During a charging process, energy from an external charger is input into the IMD. The IMD typically includes a pre-regulator that accepts the charging energy when the internal battery requires charging, but rejects the charging energy when the battery is charged to an acceptable or full level. Some of the charging energy available to the IMD is often wasted as heat, which may be caused by eddy currents in the metal can or case of the IMD. Any charging energy rejected by an IMD pre-regulator increases the heating in the case. As such, if the charging process occurs too fast, and/or if the IMD rejects the charging energy, the temperature of the IMD may quickly escalate. As such, the IMD may overheat.

Additionally, certain external chargers are battery-operated. Transmitting charging energy from an external charger typically drains the battery power. For example, during a typical charging process, the external charger transmits charging energy to an IMD, even when the IMD rejects the charging energy. Accordingly, even though the charging energy may not be accepted by the IMD, the charging energy is still being transmitted from the external charger, and thus depletes the battery of the external charger.

SUMMARY

Certain embodiments of the present disclosure provide a charging energy control system that may include an implantable medical device (IMD) and an external charger configured to transmit charging energy to the IMD in order to recharge a battery of the IMD. The IMD is configured to receive the charging energy to recharge the battery during a charging energy acceptance period and reject the charging energy during an actual charging energy rejection period. The external charger may include a charging controller configured to determine the actual charging energy rejection period, and regulate the charging energy during which the charging controller predicts a predicted charging energy rejection period of the IMD based on the actual recharging energy rejection period. The charging controller may also be configured to cease or reduce transmission of the charging energy during a charging energy conservation period that is, or temporally overlaps, at least a portion of the predicted charging energy rejection period.

In at least one embodiment, the charging controller may include an energy-rejection prediction module configured to predict the predicted charging energy rejection period of the IMD based on the actual recharging energy rejection period. The charging controller may also include a charging cycling module configured to cease or reduce the transmission of the charging energy during the charging energy conservation period.

In at least one embodiment, the charging energy conservation period may equal the predicted charging energy rejection period. In at least one other embodiment, the charging energy conservation period may be a portion, such as a fixed percentage, of the predicted charging energy rejection period. The charging energy conservation period reduces a possibility of excess heating of one or both of the IMD or the external charger. The charging energy conservation period may not overlap with any portion of the charging energy acceptance period.

The charging energy regulation period may be triggered by an end of a communication session of the IMD. The charging controller may iteratively predict subsequent predicted charging energy rejection periods and cease or reduce transmission of the charging energy during subsequent charging energy conservation periods based on subsequent actual charging energy rejection periods until the IMD experiences or expects an interfering event, such as a communication session.

The IMD may be an implantable pacemaker, an implantable cardioverter-defibrillator, a defibrillator, a cardiac rhythm management device, a neurostimulator, or an electrophysiology mapping and radio frequency ablation system.

Certain embodiments of the present disclosure provide a charging energy control method that may include transmitting charging energy from an external charger to an IMD, and receiving the charging energy from the external charger at the IMD. The receiving operation includes recharging a battery of the IMD with the received charging energy during a charging energy acceptance period, and rejecting the charging energy during an actual charging energy rejection period. The method may also include regulating the charging energy during a charging energy regulation period with a charging controller. The regulating operation may include determining the actual charging energy rejection period, predicting a predicted charging energy rejection period of the IMD based on the actual recharging energy rejection period, and ceasing or reducing transmission of the charging energy during a charging energy conservation period that is, or temporally overlaps, at least a portion of the predicted charging energy rejection period.

Certain embodiments of the present disclosure provide an external charger configured to recharge a battery of an IMD, wherein the IMD is configured to receive charging energy from the external charger to recharge the battery during a charging energy acceptance period and reject the charging energy during an actual charging energy rejection period. The external charger may include a charging controller configured to regulate the charging energy during which the charging controller determines the actual charging energy rejection period, predicts a predicted charging energy rejection period of the IMD based on the actual recharging energy rejection period, and ceases or reduces transmission of the charging energy during a charging energy conservation period that is, or temporally overlaps, at least a portion of the predicted charging energy rejection period.

DETAILED DESCRIPTION

Figure 1:
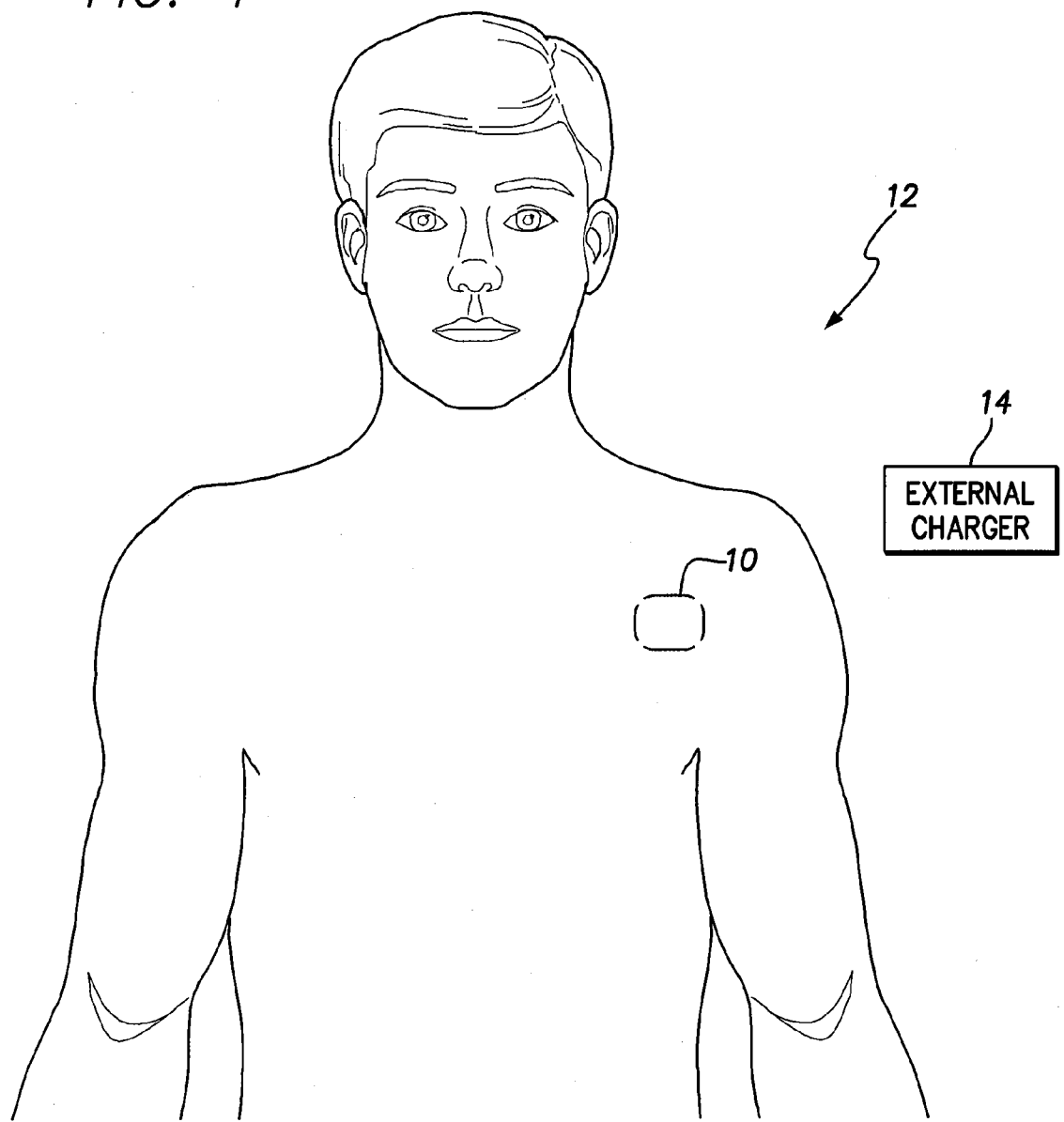
FIG. 1 illustrates an IMD implanted in a patient, according to an embodiment of the present disclosure.

FIG. 1 illustrates an IMD 10 implanted in a patient 12, according to an embodiment of the present disclosure. The IMD 10 may be one of various types of implantable devices, such as, for example, an implantable pacemaker, implantable cardioverter-defibrillator, defibrillator, cardiac rhythm management device, neurostimulator, electrophysiology mapping and radio frequency ablation system, or the like. The IMD 10 is configured to be charged by an external charger 14 that is outside of the patient 12. The external charger 14 may be part of an external programmer configured to program and communicate with the IMD 10.

As shown in FIG. 1, the IMD 10 is implanted proximate to the chest and shoulder area of the patient 12. However, the IMD 10 may be implanted at various other anatomical areas.

Figure 2:
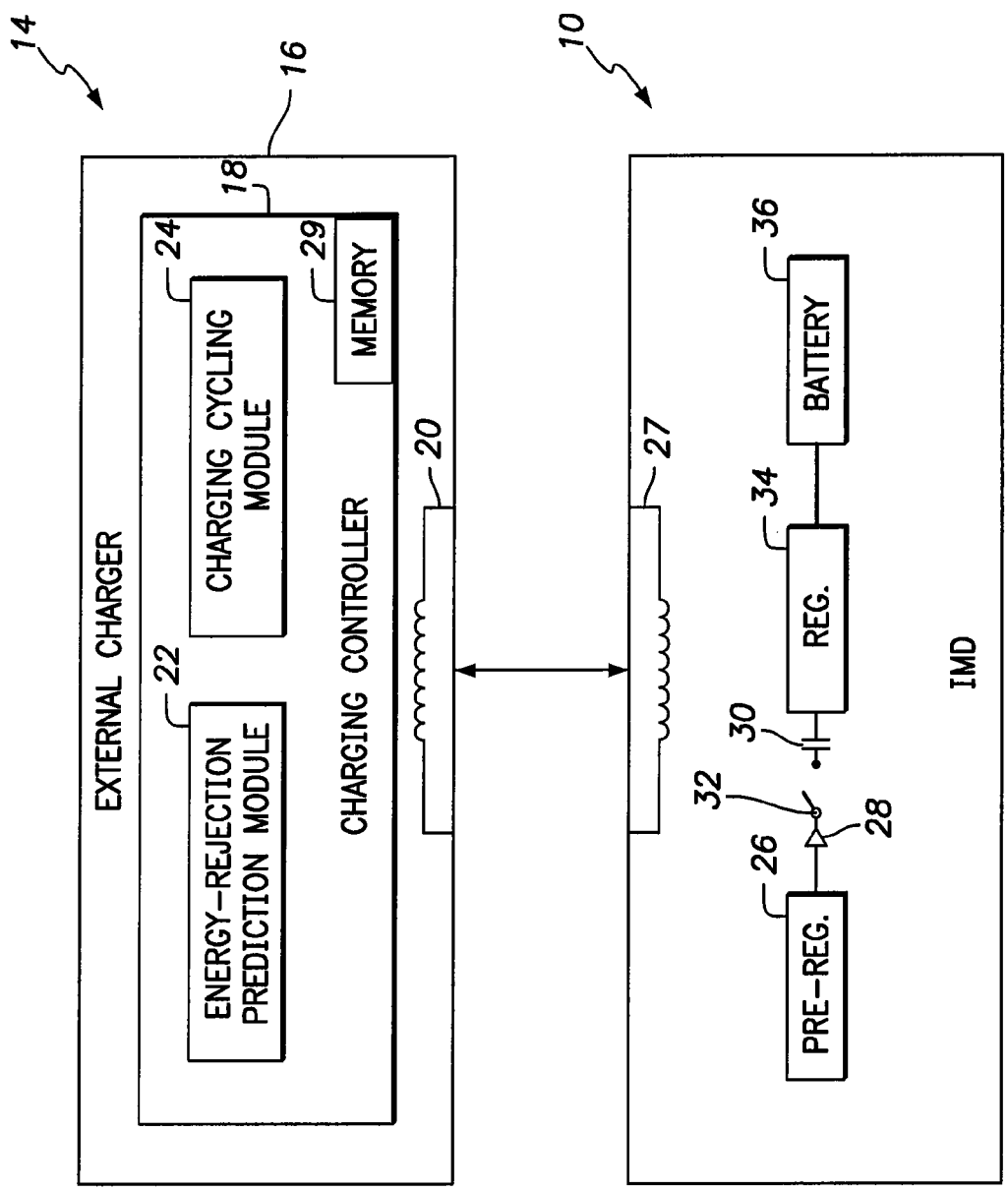
FIG. 2 illustrates a simplified block diagram of an external charger and an IMD, according to an embodiment of the present disclosure.

FIG. 2 illustrates a simplified block diagram of the external charger 14 and the IMD 10, according to an embodiment of the present disclosure. The external charger 14 includes a housing 16, which may be configured to be held by hand, that includes a charging controller 18 and a charging energy transmission coil 20. The charging controller 18 may include an energy-rejection prediction module 22, a charging cycling module 24, and a memory 29.

The IMD 10 may include a charging energy receiving coil 27 that may be electrically connected to a pre-regulator 26, which, in turn, is connected to a comparator 28 that monitors an energy state of a capacitor 30, for example. The simplified diagram shown in FIG. 2 is merely exemplary. The capacitor 30 may be a shunt capacitor, for example. A switch 32, such as a transistor switch, may be disposed between the pre-regulator 26 and the capacitor 30. The capacitor 30 may also be connected to a regulator 34, which, in turn, is connected to a battery 36. It is to be understood that not all of the components of the external charger 14 and the IMD 10 are necessarily shown in FIG. 2. Instead, FIG. 2 merely illustrates schematic representations of certain components that may be used during a charging process of the IMD 10.

In order to charge the IMD 10, the external charger 14 may be brought in close proximity to the IMD 10. For example, referring to FIGS. 1 and 2, an individual may place the external charger 14 over skin of the patient 12 that is proximate to the IMD 10. An activation switch (not shown) of the external charger 14 may be engaged in order to transmit charging energy from the transmission coil 20 into the IMD 10.

The charging energy transmitted from the transmission coil 20 is received by the receiving coil 27 of the IMD 10. The pre-regulator 26 receives the charging energy from the receiving coil 24 and monitors the charge status of the capacitor 30 through the comparator 28. If the capacitor 30 requires charging, the pre-regulator 26 closes the switch 32 so that the charging energy is sent to the capacitor 30 and stored therein. The regulator 34 monitors the charge status of the battery 36. When the charge status of the battery is low, the regulator 34 discharges stored charging energy within the capacitor 30 into the battery 36, thereby providing energy to the battery 36.

As noted, the pre-regulator 26 may monitor the charge status of the capacitor 30 through the comparator 28. The comparator 28 monitors the potential or voltage across the capacitor 30. When the comparator 28 detects a maximum or high voltage level within the capacitor 30 (in relation to a maximum voltage threshold), the pre-regulator 26 opens the switch 32 so that the charging energy is prevented from passing into the capacitor 30. When the comparator 28 detects a minimum or low voltage level within the capacitor 30 (in relation to a minimum voltage threshold), the pre-regulator 26 closes the switch 32 so that the charging energy passes into the capacitor 30, where the charging energy is stored. During the time when the switch 32 is open such that the charging energy is prevented from passing into the capacitor 30, the IMD 10 rejects the charging energy.

While the IMD 10 is shown with the capacitor 30, the switch 32, and the comparator 28, more or less capacitors, switches, and comparators may be used. For example, the pre-regulator 26 may monitor the charge status of the capacitor 30 through various other devices, circuits, and the like. In at least one embodiment, the pre-regulator 26 may be directly connected to the capacitor 30 without a comparator and switch. Also, the IMD 10 may alternatively not include any capacitor. Instead, the receiving coil 24 may be directly connected to the regulator 34, for example, which may accept and reject charging energy that is intended for the battery 36.

In order to prevent the IMD 10 from over-heating, such as through rejected charging energy, and to conserve energy, the charging controller 18 is configured to predict when the IMD 10 rejects the charging energy and cease or reduce transmission of the charging energy. The energy-rejection prediction module 22 is configured to predict time periods when the IMD 10 rejects the charging energy, and the charging cycling module 24 deactivates or reduces the charging energy transmission during at least a portion of the predicted time periods.

While shown as separate and distinct modules, the energy-rejection prediction module 22 and the charging cycling module 24 may be integrally part of a single module. For example, the charging controller 18 may include integral circuitry and/or operating instructions configured to predict periods of energy-rejection by the IMD 10 and cease transmission of the charging energy during such periods.

Figure 3:
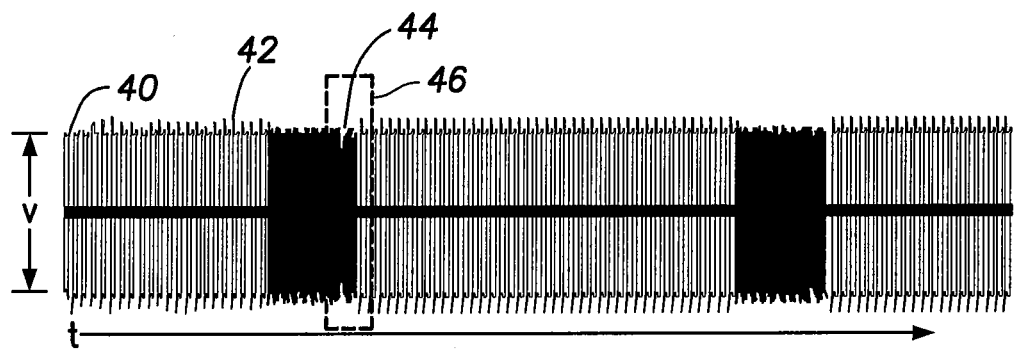
FIG. 3 illustrates a pattern for charging energy over time, according to an embodiment of the present disclosure.

FIG. 3 illustrates a pattern for charging energy 40 over time, according to an embodiment of the present disclosure. The charging energy 40 represents the charging energy available in a time varying magnetic field in an inductive charging system, for example. However, embodiments of the present disclosure may be used with non-inductive charging systems, as well. The charging energy 40 is transmitted from the external charger 14 (shown in FIGS. 1 and 2) and received by the IMD 10 (shown in FIGS. 1 and 2). The charging energy 40 may be measured as a voltage within the external device 14 and/or the IMD 10. When the charging energy 40 is at intermediate amplitude 44, the charging energy 40 is considered loaded, either by a communication from the IMD 10, or by the IMD 10 accepting the charging energy to charge the onboard battery 36 (shown in FIG. 2). When the charging energy 40 is at maximum amplitude 42, the charging energy is considered unloaded and qualified for reduction/deactivation. When the charging energy 40 is at minimum amplitude, the charging energy 40 has been reduced or deactivated. A charging energy regulation period 46 is also shown in FIG. 6.

Figure 4:
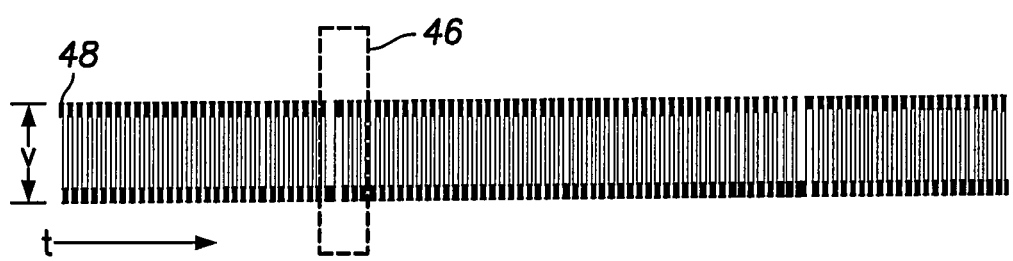
FIG. 4 illustrates demodulated representation of a magnetic field envelope of charging energy over time that is amplified to saturation, according to an embodiment of the present disclosure.

FIG. 4 illustrates a demodulated representation of a magnetic field envelope of charging energy 48 over time amplified to the point of saturation, according to an embodiment of the present disclosure. The demodulated, amplified charging energy 48 is low when the magnetic field is lowered, either by loading, or by reduction/deactivation of the charging energy 48. For example, referring to FIGS. 1 and 2, when the IMD 10 accepts charging energy, the IMD 10 allows more current to pass therethrough, which, in turn, slightly diminishes the magnetic field. As such, when the IMD 10 rejects the charging energy, the magnetic field strength may be greater than when the IMD 10 accepts the charging energy. The external charging device 14 may be configured to detect the changes in magnetic field strength to determine when the IMD 10 is accepting and rejecting charging energy. For example, the external charging device 14 may include a sensing coil in communication with the charging controller 18. The sensing coil may be used to detect changes in magnetic field strength and/or voltage. Also, the external charging device 14 may alternatively detect changes in the magnetic field strength and/or voltage using the same coil used to transmit energy to the IMD 10

Figure 5:
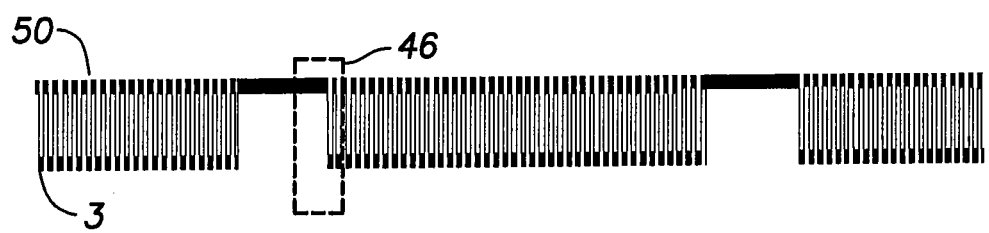
FIG. 5 illustrates a pattern for charging energy output by an external charger, according to an embodiment of the present disclosure.

FIG. 5 illustrates a pattern for charging energy 50 output by the external charger 14 (shown in FIG. 1), according to an embodiment of the present disclosure. The external charger 14 may control the charging energy 50 at a desired level based on communications and charging periods. The charging energy 50 shown in FIG. 5 represents the actual charging energy that is output by the external charger 14 at various points during operation of external charger in relation to the IMD 10. For example, the charging energy 50 is output by the external charger during periods of time when the IMD 10 accepts the charging energy. The external charger 14 may detect a magnetic field of the IMD 10. The magnetic field changes when the IMD 10 accepts charging energy, and rejects charging energy. Based on the detected changes, the external charger 14 measures one or more periods when the IMD 10 rejects the charging energy, and uses the measured period(s) to predict future periods when the IMD 10 rejects the charging energy. During the predicted periods, the external charger 14 may cease or reduce output charging energy, thereby conserving energy and reducing the susceptibility of overheating the IMD 10.

Figure 6:
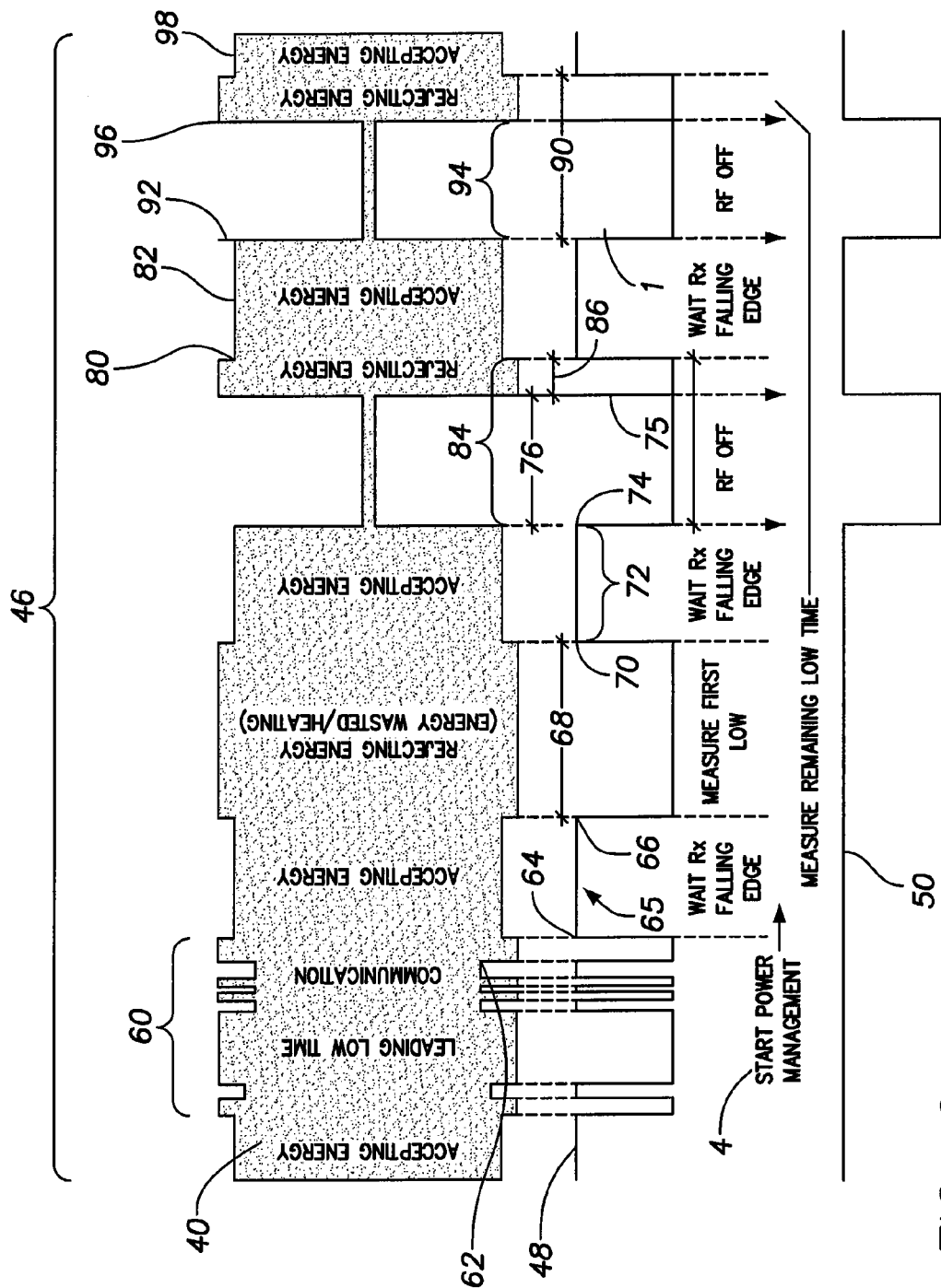
FIG. 6 illustrates a charging energy regulation period, according to an embodiment of the present disclosure.

FIG. 6 illustrates the charging energy regulation period 46, according to an embodiment of the present disclosure. Referring to FIGS. 1-6, the charging energy regulation period 46 may be triggered by a communication session 60 of the IMD 10. For example, when the IMD 10 communicates with an external programmer (not shown) and/or the external charger 14, such as by receiving data from the external programmer, or sending data thereto, the charging energy regulation period 46 may be triggered. After the communication session 60, the IMD 10 may accept charging energy from the external device 14 during a first energy receiving stage 62.

In order to begin regulation, management, or otherwise control of the charging energy 40, the communication session 60 first ceases. In general, the charging energy regulation period 46 begins when no interfering system events, such as communication from the IMD 10, occur or are expected. The interfering system events may interfere with detection of demand of charging energy. Alternatively, the charging energy regulation may occur at any time, even during a communication session, such as in windows between data pack transmissions.

Once the communication session 62 ends, the charging energy regulation period 46 is initiated at time 64 when the IMD 10 begins to accept charging energy. The IMD 10 only accepts charging energy for discrete periods of time, referred to as a charging energy acceptance period 65 that lasts from time 64 until time 66. The charging energy acceptance period 65 is the discrete period of time when the IMD 10 accepts the charging energy from the external charger 14. At the beginning of the charging energy regulation period 46, the IMD 10 accepts energy from the external charger 14 during the charging energy acceptance period 65. For example, with reference to FIG. 2, the pre-regulator 26 may close the switch 32 so that the charging energy is provided to the capacitor 30 and/or the battery 36.

The IMD 10 continues to accept the charging energy from time 64 until time 66. After time 66, the IMD 10 begins rejecting the charging energy and continues to do so during an actual charging energy rejection period 68 that lasts from time 66 until time 70. The actual charging energy rejection period 68 is a discrete period of time in which the IMD 10 rejects energy output from the external charger 14. The IMD 10 rejects the energy during the actual charging energy rejection period 68 because the IMD 10 may be fully-charged, and may not be able to utilize any additional energy. The IMD 10 also temporarily rejects charge when the capacitors in the voltage regulation circuit that supplies power to the batter are fully charged. As the capacitors discharge (to fill the battery), the IMD 10 again accepts external charging energy.

The charging controller 18 detects and monitors the length of the actual charging energy rejection period 68 in order to predict later charging energy rejection periods. For example, the energy-rejection prediction module 22 may detect the time period of the actual charging energy rejection period 68 by monitoring a change in the magnetic field and/or voltage of the charging energy 40 received by the IMD 10. In order to detect the change in the magnetic field and/or voltage, the charging controller 18 may include, or be in communication with, a separate and distinct sensing coil that is configured to detect the magnetic field and/or the voltage of the charging energy 40 at the IMD 10. Also, the external charging controller 18 may alternatively be in communication with a module that detects changes in the magnetic field strength and/or voltage using the same coil used to transmit energy to the IMD 10. The charging controller 18, such as through the energy-rejection prediction module 22, stores the length of the time of the actual charging energy rejection period 68, such as within the memory 29 (shown in FIG. 2). The charging controller 18 determines the time 70 based on the change in the measured magnetic field and/or the voltage of the charging energy 40 in comparison to the field and/or voltage during the charging energy acceptance period 65.

At the end of time 70, the IMD 10 is ready to accept charging energy again and thus a subsequent charging energy acceptance period 72 occurs between the time 70 and a time 74. The charging energy acceptance period 72 is a discrete period of time subsequent to the charging energy acceptance period 65 when the IMD 10 accepts the charging energy from the external charger 14. During the charging energy acceptance period 72, the IMD 10 once again accepts the charging energy 40 from the external charger 14.

After time 74, the IMD 10 reaches an internal state in which the IMD 10 begins to reject the charging energy, as the IMD 10 may be fully-charged and unable to utilize additional charging energy. The IMD 10 continues to reject the charging energy during a subsequent actual charging energy rejection period 84, which is the discrete period of time subsequent to the charging energy acceptance period 72 in which the IMD 10 actually rejects any charging energy output from the external charger 14.

Based on the measured and stored time period of the first actual charging energy rejection period 68, the charging controller 18, such as through the energy-rejection prediction module 22, predicts a potential or candidate length of time of the subsequent actual charging energy rejection period 84. The predicted charging energy rejection period, which may or may not exactly coincide with the actual charging energy rejection period 84, represents the potential or candidate period of time that the controller 18 predicts, through various calculation techniques, that the IMD 10 will remain in a state in which the IMD 10 rejects (does not accept) additional charge. The energy-rejection prediction module 22 uses the actual charging energy rejection period 68 to base a prediction for the subsequent actual charging energy rejection period 84. For example, the energy-rejection prediction module 22 may be programmed to determine that any subsequent charging energy rejection period will be between 90%-120% of a measured preceding actual charging energy rejection period. However, the energy-rejection prediction module 22 may be programmed to determine subsequent charging energy periods that are greater or less than between 90%-120%.

After the energy-rejection prediction module 22 predicts a length of the actual charging energy rejection period 84, the charging controller 18, such as through the charging cycling module 24, ceases or reduces transmitting charging energy during at least a portion of the actual charging energy rejection period 84 so that the IMD 10 does not overheat through wasted charging energy and also to conserve charging energy. For example, the charging cycling module 24 may open a switch that controls transmission of the charging energy from the coil 20.

The actual charging energy rejection period 84 may be longer than a charging energy conservation period 76, which is subsumed by the actual charging energy rejection period 84. The charging energy conservation period 76 represents the discrete period of time in which the external charger 14 ceases or reduces emitting charging energy, based on the prediction charging energy rejection period. As such, the charging energy conservation period 76 temporally overlaps at least a portion of the predicted charging energy rejection period. For example, the charging energy conservation period 76 may be a portion of the predicted charging energy rejection period.

During the charging energy conservation period 76, the external charger 14 may cease or otherwise reduce transmission of the charging energy. At time 75, the controller 18 reactivates transmission of charging energy. The external charger 14 re-activates transmission of the charging energy during an overlap time period 86 after the end of the charging energy conservation period 76, and before the IMD 10 begins accepting the charging energy 40 again. The overlap time period 86 represents the period that the external charger 14 transmits energy even though the IMD 10 is currently rejecting the energy, so that the external charger 14 will be transmitting charging energy at the instant when the IMD 10 begins accepting the charging energy again.

In at least one embodiment, the charging cycling module 24 may cease transmission of charging energy from the external charger 14 for an entire duration of the predicted charging energy rejection period that relates to the actual charging energy rejection period 84 (although the predicted charging energy rejection period that relates to the actual charging energy rejection period 84 is based on the actual charging energy rejection period 68, as described above). For example, the charging energy rejection period 84 may equal the charging energy conservation period 76. Optionally, the charging cycling module 24 may cease transmission of the charging energy for a shorter duration of the predicted charging energy rejection period 84, so that the charging energy 40 is transmitted when the IMD 10 once again begins accepting the charging energy 40 at time 80 during another charging energy acceptance period 82.

The charging controller 18 may calculate the charging energy conservation period 76 as a fixed portion, percentage, ratio, or the like of the predicted charging energy rejection period 84. For example, the charging energy conservation period 76 may be between 50-99% of the predicted charging energy rejection period 84. Alternatively, the charging energy conservation period 76 may be more or less than between 50-99% of the predicted charging energy rejection period 84.

During the actual charging energy rejection period 84, the charging controller 18 measures the actual time period of the actual charging energy rejection period 84. The actual charging energy rejection period 84 may be shorter or longer than the predicted charging energy rejection period related to the actual charging energy rejection period 84. As such, the charging controller 18 monitors the actual time period of the actual charging energy rejection period 84 so as to base subsequent predictions for a charging energy rejection period. The charging controller 18 stores the length of the full actual charging energy rejection period 84 and uses the length of the full actual charging energy rejection period 84 to predict a subsequent predicted charging energy rejection period that relates to an actual charging energy rejection 90.

Once the charging energy acceptance period 82 ends at time 92, the charging controller 18, such as through the charging cycling module 24, may cease or otherwise reduce transmission of the charging energy 40, such as during a charging energy conservation period 94, which may be shorter than the full charging energy rejection period 90, similar to as explained above. Again, the charging controller 18 may re-activate the transmission of the charging energy 40 at a time 96 that occurs before the IMD 10 begins accepting the charging energy 40 during another charging energy acceptance period 98.

As explained above, the external charger 14 (such as through the energy-rejection prediction module 22) predicts the charging energy rejection period 84 based on the length of the measured charging energy rejection period 68. The external charger 14 (such as through the charging cycling module 24) then ceases or reduces the transmitted charging energy during the calculated charging energy conservation period 76, which may be a pre-defined portion of the predicted charging energy rejection period 84. The external charger 14 then determines the subsequent charging energy rejection period 90 based on the actual length of the charging energy rejection period 84. The predicted and/or actual charging energy rejection period 90 may be greater or less than the actual charging energy rejection period 84. The external charger 14 ceases or reduces the transmitted charging energy during the calculated charging energy conservation period 94, which may be a pre-defined portion of the predicted charging energy rejection period 90.

The process then continues until an interfering event, such as a communication session, occurs or is expected. The charging energy regulation period 46 may be an iterative process that repeats until the IMD 10 transitions to a communication session, such as the communication session 60. When the external charger 14 detects a communication session 60, the process begins anew.

Optionally, instead of ceasing transmission of the charging energy during the periods 76 and 94, for example, the charging controller 18 may reduce the power level of the charging energy. For example, the charging controller 18 may reduce the power level to 50% or less than the normal transmission power level.

While detecting time periods of charging energy rejection, the charging controller 18 may ignore noise, such as brief energy spikes, that may be caused by changes in output charging energy, for example.

Thus, embodiments of the present disclosure provide a system and method of ceasing, minimizing, or otherwise reducing transmission of the charging energy 40 during periods when the IMD 10 rejects the charging energy, thereby conserving energy within the external charger 14 and preventing the IMD 10 from overheating. The external charger 14 detects and measures the length of the actual charging energy rejection periods and uses such information to predict lengths of subsequent predicted charging energy rejection periods. Based on the predicted charging energy rejection periods, the external charger 14 ceases, minimizes, or otherwise reduces transmission of the charging energy.

Embodiments of the present disclosure provide a system and method of controlling the charging energy transmitted by the external charger 14. Because the external charger ceases or reduces the transmission of the charging energy during one or more charging energy conservation periods, the IMD 10 and the external charger 14 are less likely to overheat. Moreover, the battery-life of the external charger 14 is increased. As such, the charging capacity of the external charger 14 is increased, as it wastes little to no charging energy that would otherwise be rejected by the IMD 10.

Embodiments of the present disclosure provide external chargers that are configured to detect and process use of charging energy by IMDs and deliver the charging energy during charging energy acceptance periods. The external chargers may refrain from delivering (or reduce the power level of) the charging energy during at least portions of charging energy rejection periods.

As noted above, the charging controller 18 of the external charger 14 may include the energy-rejection prediction module 22 and the charging cycling module 24. The energy-rejection prediction module 22 may be configured to predict charging energy rejection periods of the IMD 10, as described above. The charging cycling module 24 may be configured to cease or reduce transmission of the charging energy based on the predicted charging energy predictions.

The charging controller 18, including the energy-rejection prediction module 22 and the charging cycling module 24, may generally include or represent hardware and associated instructions (for example, software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The charging controller 18 may include a programmable microcontroller that controls the various modes of energy-rejection prediction, charging cycling (such as cycling between a charging energy transmission state and refraining from transmitting charging energy), and the like. The microcontroller may include a microprocessor, or equivalent control circuitry, designed specifically for controlling operation and may further include RAM or ROM memory, logic and timing circuitry, state machine circuitry, and I/O circuitry. The charging controller 18 includes the ability to process or monitor input signals (data) as controlled by a program code stored in memory. The details of the design and operation of the charging controller 18 are not critical to the present disclosure. Rather, any suitable microcontroller, for example, may be used.

Figure 7:
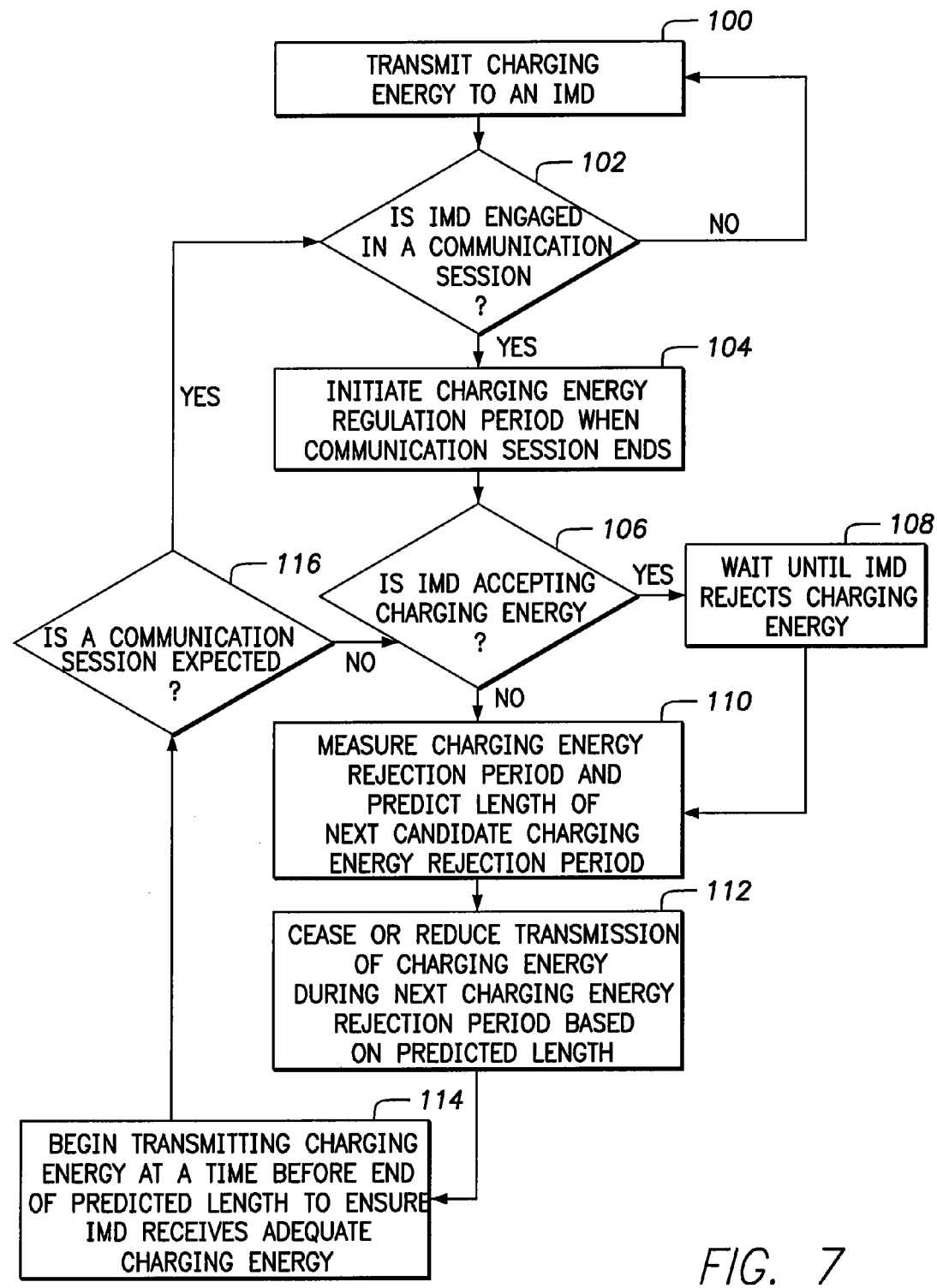
FIG. 7 illustrates a flow chart of a method of controlling charging energy transmitted to an IMD, according to an embodiment of the present disclosure.

FIG. 7 illustrates a flow chart of a method of controlling charging energy transmitted to an IMD, according to an embodiment of the present disclosure. The method begins at 100, in which charging energy is transmitted from an external charger to the IMD. At 102, it is determined whether the IMD is engaged in a communication session. If not, the method returns to 100. If, however, the IMD is engaged in a communication session, the method proceeds to 104, in which a charging energy regulation period is initiated when the communication session ends.

At 106, it is then determined whether the IMD is accepting charging energy. If the IMD is accepting the charging energy, the method proceeds to 108, in which the external charger continues to supply the charging energy device and waits until the IMD rejects the charging energy. When the IMD rejects the charging energy, the method proceeds to 110, in which the external charger measures an actual charging energy rejection period and predicts a length of the next charging energy rejection period based on the length of the actual charging energy rejection period. Then, at 112, the external charger ceases or reduces transmission of the charging energy during the next charging energy rejection period based on the predicted length of the charging energy rejection period.

At 114, the external charger may begin transmitting charging energy at a time before the end of the predicted length to ensure that the IMD receives adequate charging energy (for example, the ensure that the IMD will be full-charged). The method then continues to 116, in which it is determined whether a communication session is expected. If not, the process returns to 106. If, however, a communication session is expected, the process returns to 102.

Figure 8:
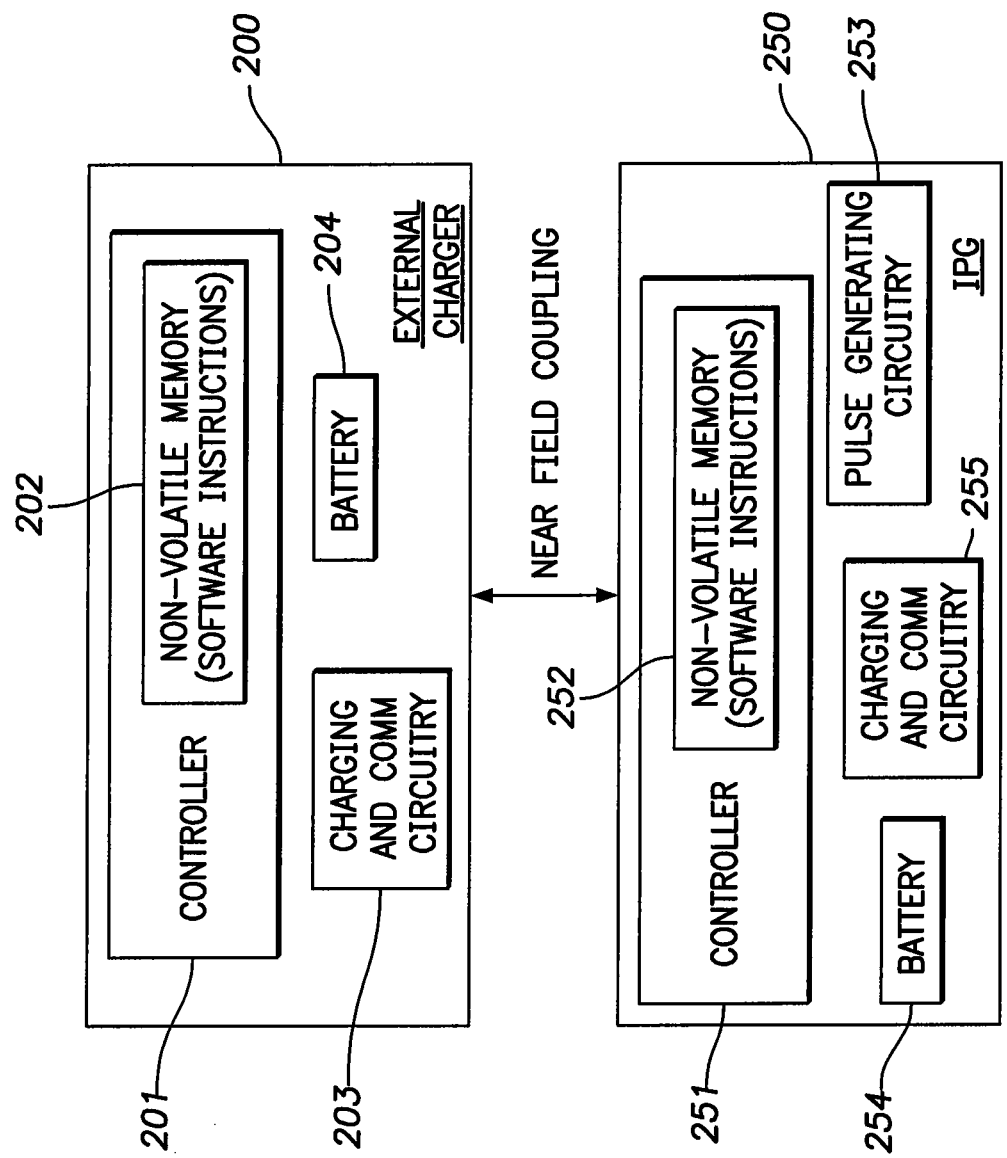
FIG. 8 illustrates a block diagram of an external charging device and an implantable pulse generator, according to an embodiment of the present disclosure.

FIG. 8 illustrates a block diagram of an external charger 200 and an implantable pulse generator (IPG) 250, according to an embodiment of the present disclosure. The IPG 250 is an example of an IMD, such as any of the IMDs described above. For example, the IPG 250 may be a neurostimulator.

Neurostimulators are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, and the like.

Neurostimulators generally include a pulse generator and one or more leads. The pulse generator may include a metallic housing that encloses circuitry for generating the electrical pulses, control circuitry, communication circuitry, a rechargeable battery, recharging circuitry, and the like. The pulse generation circuitry may be coupled to one or more stimulation leads through electrical connections provided in a "header" of the pulse generator. Stimulation leads typically include multiple wire conductors enclosed or embedded within a lead body of insulative material. Terminals and electrodes are located on the proximal and distal ends of the leads. The conductors of the leads electrically couple the terminals to the electrodes. The electrical pulses from the pulse generator are conducted through the leads and applied to patient tissue by the electrodes of the leads.

Recharging of the IPG 250 may occur by near-field coupling of a coil in the IPG 250 with a coil of the external charger 200. The external charger 200 radiates power from its coil which induces current in the coil of the IPG 250. The recharging circuitry of the IPG 250 rectifies the induced current and charges the battery 254 of the IPG 250, subject to various regulation circuitry.

The external charger 200 may include a controller 201 (for example, any suitable commercially available microcontroller) for controlling the operations of the external charger 200 according to instructions stored in non-volatile memory 202. The external charger 200 may be powered by the battery 204, which may be a rechargeable lithium ion battery. The external charger 200 may also include charging and communication circuitry 203. The controller 201 and/or the charging and communication circuitry 203 may include the charging controller 18, shown in FIG. 1. The charging and communication circuitry 203 may be adapted, in some embodiments, to electrically couple to a coil of an external wand that is held, during charging, by a patient about his/her body immediately adjacent to the implant site of the IPG 250. Alternatively, the coil may be integrated in the same device package with the circuitry of the external charger 200. The charging and communication circuitry 203 drives the coil using a suitable RF signal for charging purposes. The charging and communication circuitry 203 also drives the coil using a suitable modulated RF signal to communicate data to the IPG 250. The external charger 200 may also be adapted for use as a controller to control the operations of the IPG 250 by communicating suitable control parameters using the circuitry 203.

The IPG 250 may include a controller 251 (for example, any suitable commercially available microcontroller) for controlling the pulse generating and other operations of the IPG 250 according to instructions stored in non-volatile memory 252. The IPG 250 may include pulse generating circuitry 253 for generating stimulation pulses for delivery to tissue of the patient. The pulse generating circuitry 253 may include one or multiple pulse sources. Also, the pulse generating circuitry 253 may operate according to constant voltage stimulation, constant current stimulation, or any other suitable mode of operation. The IPG 250 may be adapted for spinal cord stimulation, peripheral nerve stimulation, peripheral nerve field stimulation, deep brain stimulation, cortical stimulation, gastric pacing, cardiac therapies, and/or the like.

The various components of the IPG 250 are powered by a battery 254, such as a lithium ion rechargeable battery. The battery 254 is recharged by converting RF power radiated from the external charger 200. Charging and communication circuitry 255 may include a coil for near-field coupling with the coil of the external charger 200. When the external charger 200 radiates RF power using its coil, the inductive coupling between the coil of the external charger 200 with the coil of the IPG 250 causes current to be induced in the coil of the IPG 250. The circuitry 255 uses the induced current to charge the battery 254. Also, the circuitry 255 may use the same coil to communicate with the external charger 200.

Figure 9:
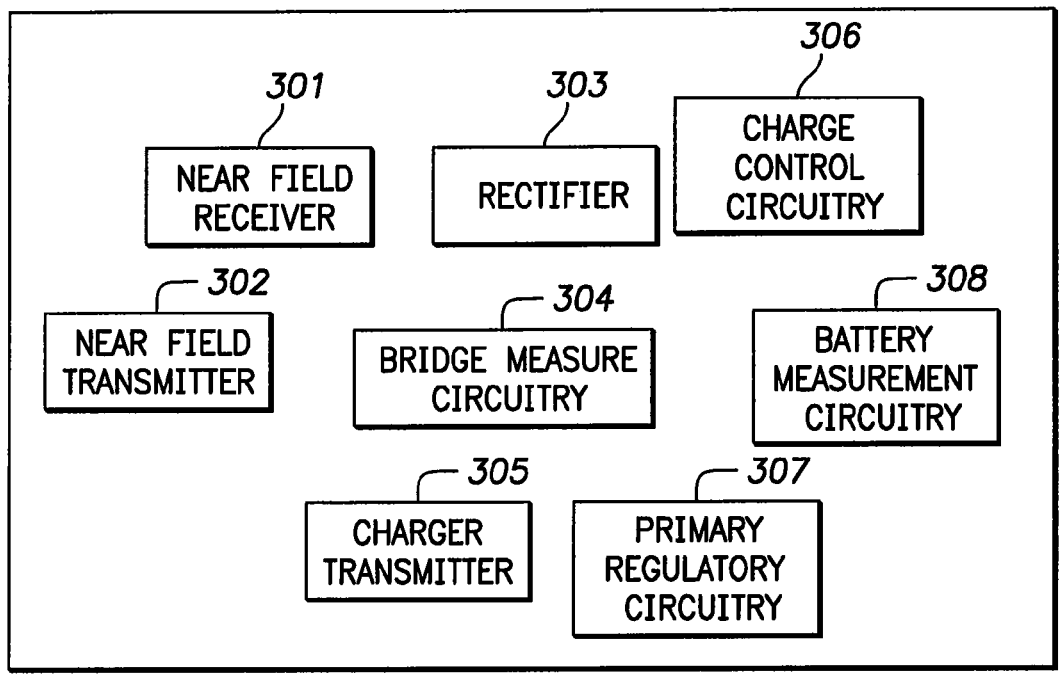
FIG. 9 illustrates a block diagram of charge control and communication circuitry of an implantable pulse generator, according to an embodiment of the present disclosure.

FIG. 9 illustrates a block diagram of the charge control and communication circuitry 255 of the IPG 250, according to an embodiment of the present disclosure. The circuitry 255 may include coil and bridge rectifier circuitry 303. The coil of circuitry 303 may be used both for charging operations and for communication with the external charger 200. Near field receiver 301 is coupled to the coil. A receiver 301 demodulates data when a carrier at an appropriate frequency is detected. The receiver 301 communicates a serial data stream to controller the 251. A near field transmitter 302 receives a serial data stream from controller 251 and generates a modulated RF signal for application to a coil to communicate data to the external charger 200. Signal modulation and demodulation may, alternatively, be implemented in software executing on the controller 251. In at least one embodiment, the near field receiver 301 and the transmitter 302 do not operate when charging operations are taking place. Accordingly, a charger transmitter 305 is employed to provide charging status messages to the external charger 200 when charging is occurring.

Bridge measure circuitry 304 measures the output voltage of the circuitry 255 for control of charging operations. Primary regulatory circuitry 307 operates to control charging operations in response to the measurement signal from the circuitry 304. When the output voltage is relatively low, regulatory circuitry 307 permits circuitry 255 to absorb RF power. When the output voltage is relatively high, the coil is shorted to ground to prevent absorption of RF power.

Charge control circuitry 306 controls the charging of battery 254. Charge control circuitry 306 uses the measurement functionality of battery measurement circuitry 308 to detect the state of battery 254. Battery measurement circuitry 308 may measure the battery voltage, charging current, battery discharge current, and/or the like. Using the battery voltage measurement of the circuitry 308, the charge control circuitry 306 may prevent battery charging when an end-of-life (EOL) state has been reached for the battery 254.

Figure 10:
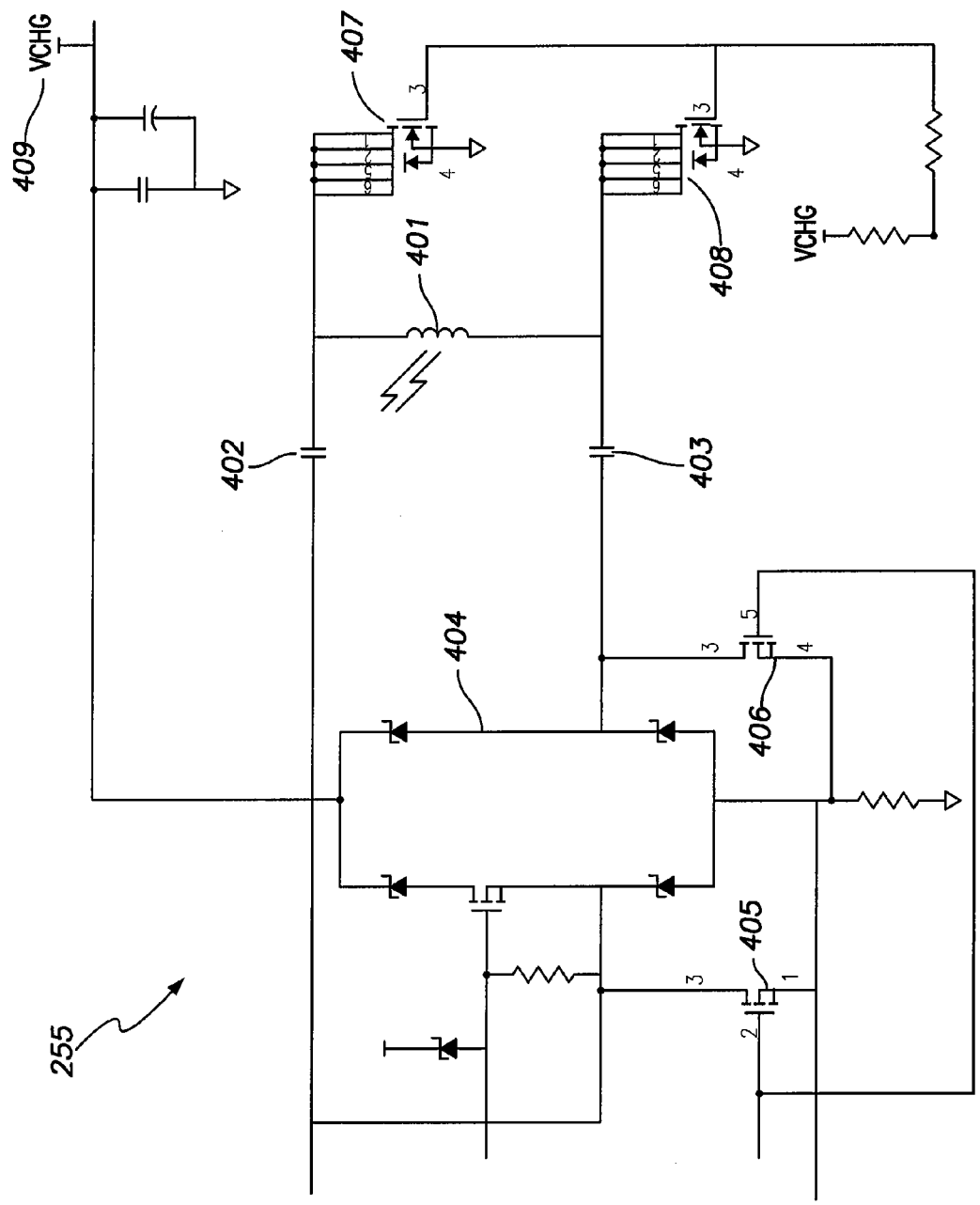
FIG. 10 illustrates charging and communication circuitry of an implantable pulse generator, according to an embodiment of the present disclosure.

FIG. 10 illustrates the charging and communication circuitry 255 of the IPG 250 (shown in FIG. 8), according to an embodiment of the present disclosure. The circuitry 255 may include a coil 401 for inductively coupling with the coil of the external charger 200. Specifically, the coil 401 and capacitors 402 and 403 may be tuned to capture RF power at one or more frequencies. In at least one embodiment, the coil 401 and capacitors 402 and 403 are tuned to receive power at a first RF frequency from external charger 200 and at a second RF frequency from a separate physician-patient programmer device (not shown).

The RF power is rectified by bridge rectifier 404. The output of the rectifier 404 is shown in FIG. 3 as node VCHG 409. The voltage on VCHG 409 is used to charge the battery assuming all necessary conditions are met. FETs 407 and 408 may be used by primary regulatory circuitry 307 to regulate the voltage on VCHG 409 during charging operations. In at least one embodiment, the primary regulatory circuitry 307 employs a band-gap comparison to regulate the voltage on VCHG 409. When the voltage is below the bottom threshold value (for example, 4.77V) of the band-gap, regulatory circuitry 307 turns off FETs 407 and 408 and coil 401 absorbs RF power. When the voltage is above the top threshold value (for example, 4.93V) of the band-gap, the regulatory circuitry 307 turns on FETs 407 and 408 to short coil 401 to ground, thereby preventing absorption of RF power. Charge control circuitry 306 uses FETs 405 and 406 to respond to an error condition or to prevent an over-voltage condition on VCHG 409. In at least one embodiment, when the voltage on VCHG 409 is above approximately 6.5V, charge control circuitry 306 clamps the bridge inputs using FETs 405 and 406 to ground to stop energy absorption by coil 401 as a redundant safety mechanism.

During charging operations, status messages may be communicated by charger transmitter 305 using FETs 405 and 406. The one-way communication may occur by controlling a 3 kHz modulation of coil 401 by charger transmitter 305. When communication of a status message is desired, charger transmitter 305 toggles its output to FETs 405 and 406. Error conditions and a charge-complete condition are examples of charging states that may be communicated using charger transmitter 305. The IPG 150 and the external charger 150 described with respect to FIGS. 8-10 may be further described in U.S. Pat. No. 8,332,040, entitled "External Charging Device for Charging an Implantable Medical Device and Methods of Regulating Duty of Cycle of an External Charging Device," which is hereby incorporated by reference in its entirety.

As noted above, FIGS. 8-10 illustrate examples of an external charger and an IMD, such as the IPG 250. However, embodiments of the present disclosure may be used with various other IMDs or IPG architectures, such as implantable pacemakers.

Figure 11:
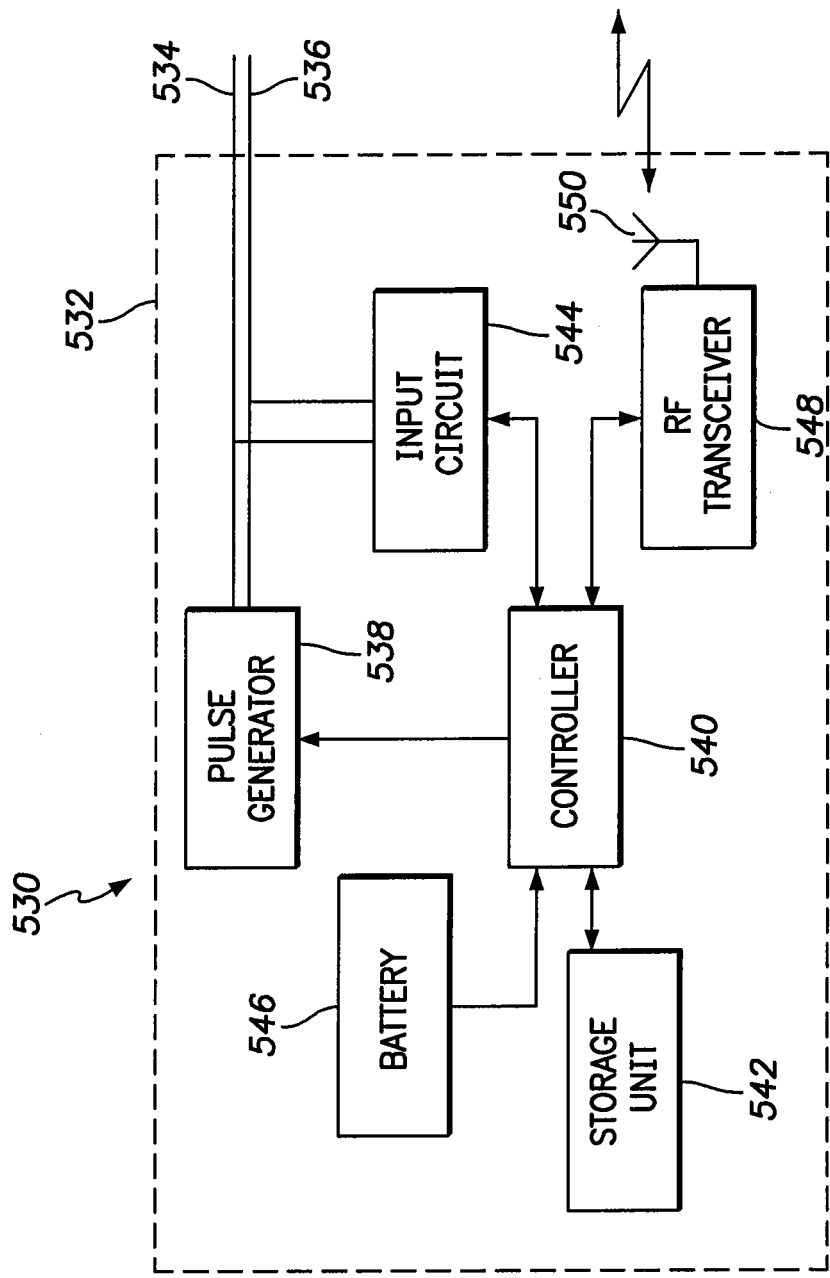
FIG. 11 illustrates a functional block diagram of an IMD, according to an embodiment of the present disclosure.

FIG. 11 illustrates a functional block diagram of an IMD 530, according to an embodiment of the present disclosure. The IMD 530 includes a housing 532 that is hermetically sealed and biologically inert. The housing 532 may be conductive and may thus serve as an electrode. The IMD 530 may be connectable to one or more leads, such as a ventricular lead 534 that is configured to be implanted in a right ventricle of the heart and an atrial lead 536 that is configured to be implanted in a right atrium of the heart. The leads 534 and 536 may include one or more electrodes, such as a tip electrode or a ring electrode that may be configured to measure impedance, measure cardiac signals, and/or transmit pacing pulses for causing depolarization of cardiac tissue adjacent to the electrodes. The pacing pulses are generated by a pace pulse generator 538 in response to directions provided from a controller or controlling circuit 540 that may include a microprocessor. The controller 540 is configured to control parameters, such as pace pulse parameters. The pace pulse parameters may include output voltage and pulse duration, for example. An example of the electronics within the IMD 530 are described below in more detail.

A storage unit 542 may be connected to the controller 540. The storage unit 542 may include a random access memory (RAM), a non-volatile memory, such as a read-only memory (ROM), a scratchpad memory, and the like. Detected signals from the patient's heart may be processed by an input circuit 544 and forwarded to the controller 540 for use in logic timing determination. The IMD 530 may be powered by a battery 546, which supplies electrical power to all active electrical components of the pacemaker.

The IMD 530 may include an RF transceiver 548 for wireless communication of signals to/from an external programmer, a patient care assembly, and the like. Medical personnel may prefer to monitor and/or adjust parameters of the IMD 530 or to perform reprogramming. The transceiver 548 may be connected to an antenna 550.

Figure 12:
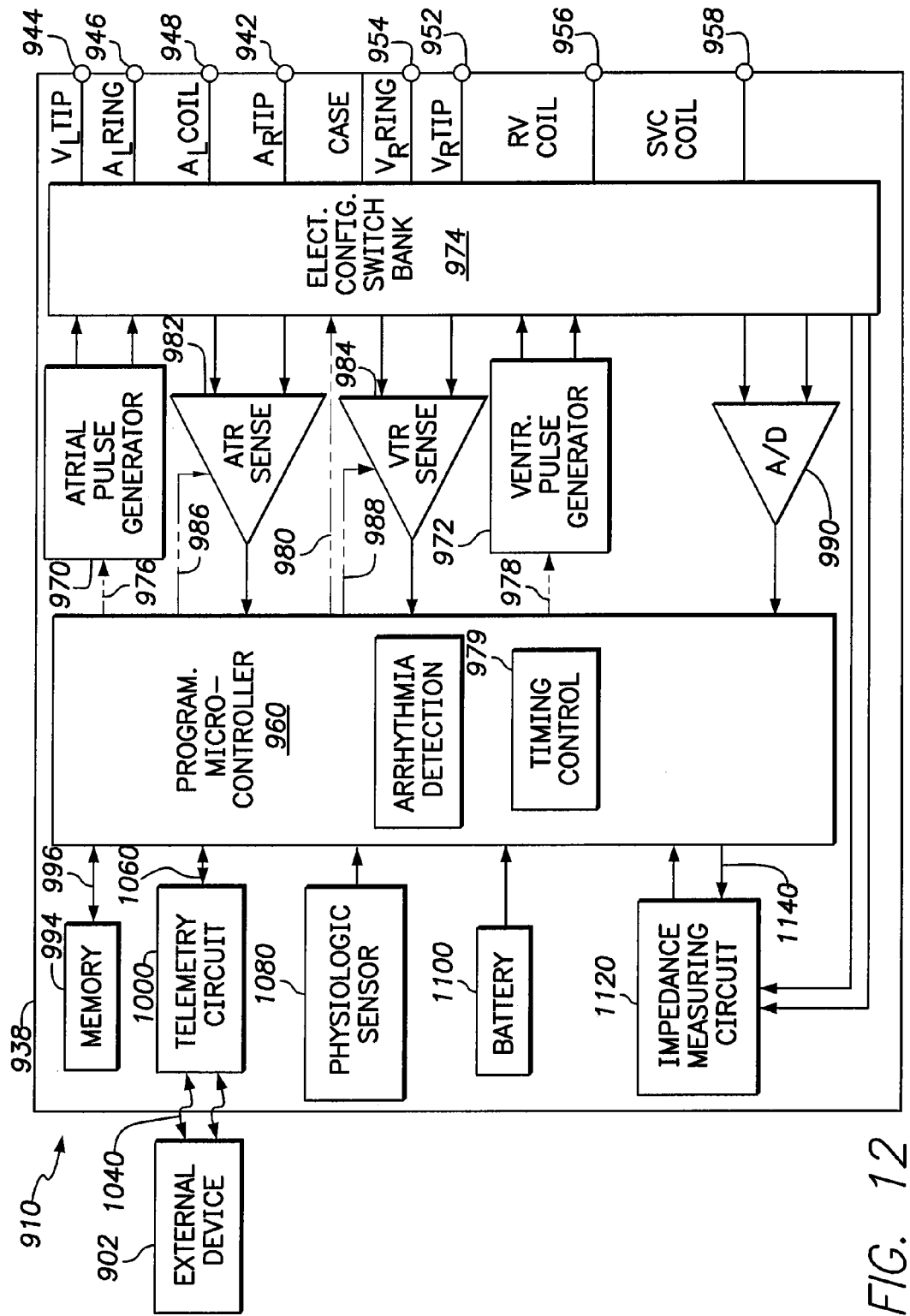
FIG. 12 illustrates a block diagram of exemplary internal components of an IMD, according to an embodiment of the present disclosure.

FIG. 12 illustrates a block diagram of exemplary internal components of an IMD 910, according to an embodiment of the present disclosure. It is to be noted that the IMD 910 is but one example of an IMD that may be used with embodiments of the present disclosure. Various other IMDs may be used in place of the IMD 910. The IMD 910 is for illustration purposes only, and it is understood that the circuitry could be duplicated, eliminated or disabled in any desired combination to provide a device capable of treating patient anatomy with cardioversion, defibrillation and/or pacing stimulation. The IMD 910 includes a housing 938, which is shown schematically in FIG. 12. The housing 938 is often referred to as the "can", "case" or "case electrode" and may be programmably selected to act as the return electrode for all "unipolar" modes. The housing 938 may further be used as a return electrode alone or in combination with one or more of the coil electrodes for shocking purposes. The housing 938 further includes a connector (not shown) having a plurality of terminals, 942, 952, 954, 956 and 958 (shown schematically and, for convenience, the names of the electrodes to which they are connected are shown next to the terminals). A right atrial tip terminal ($A_R$ TIP) 942 is adapted for connection to an atrial tip electrode and a right atrial ring terminal may be adapted for connection to a right atrial ring electrode. A left ventricular tip terminal ($V_L$ TIP) 944, a left atrial ring terminal ($A_L$ RING) 946, and a left atrial shocking terminal ($A_L$ COIL) 948 are adapted for connection to a left ventricular ring electrode, a left atrial tip electrode, and a left atrial coil electrode, respectively. A right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958 are adapted for connection to a right ventricular tip electrode, right ventricular ring electrode, an RV coil electrode, and an SVC coil electrode, respectively.

The IMD 910 includes a programmable microcontroller 960 which controls operation. The microcontroller 960 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by program code stored in memory. The details of the design and operation of the microcontroller 960 are not critical to the invention. Rather, any suitable microcontroller 960 may be used that carries out the functions described herein. Among other things, the microcontroller 960 receives, processes, and manages storage of digitized cardiac data sets from the various sensors and electrodes. For example, the cardiac data sets may include pressure data, heart sound data, and the like.

The IMD 910 includes an atrial pulse generator 970 and a ventricular/impedance pulse generator 972 to generate pacing stimulation pulses for delivery by the right atrial lead, the right ventricular lead, and/or the coronary sinus lead via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry 979 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuit 982 and ventricular sensing circuit 984 may also be selectively coupled to the right atrial lead, coronary sinus lead, and the right ventricular lead, through the switch 974 for detecting the presence of cardiac activity in each of the four chambers of the heart. Accordingly, the atrial (ATR SENSE) and ventricular (VTR SENSE) sensing circuits, 982 and 984, may include dedicated sense amplifiers, multiplexed amplifiers or shared amplifiers. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

Cardiac signals are also applied to the inputs of an analog-to-digital (A/D) data acquisition system 990. The data acquisition system 990 is configured to acquire signals, convert the raw analog data into a digital signal, and store the digital IEGM signals in memory 994 for later processing and/or telemetric transmission to an external device 902. The data acquisition system 990 is coupled to the right atrial lead, the coronary sinus lead, and the right ventricular lead through the switch 974 to sample cardiac signals across any combination of desired electrodes.

The microcontroller 960 is coupled to memory 994 by a suitable data/address bus 996, wherein the programmable operating parameters used by the microcontroller 960 are stored and modified, as required, in order to customize the operation of IMD 910 to suit the needs of a particular patient. The memory 994 also stores data sets (raw data, summary data, histograms, etc.), such as the IEGM data, heart sound data, pressure data, SvO2 data and the like for a desired period of time (e.g., 1 hour, 24 hours, 1 month, etc.). The memory 994 may store instructions to direct the microcontroller 960 to analyze the cardiac signals and heart sounds, identify characteristics of interest, and derive values for predetermined statistical parameters. The IEGM, pressure, and heart sound data stored in memory 994 may be selectively stored at certain time intervals, such as 5 minutes to 1 hour periodically or surrounding a particular type of arrhythmia of other irregularity in the heart cycle. For example, the memory 994 may store data for multiple non-consecutive 10 minute intervals.

The pacing and other operating parameters of the IMD 910 may be non-invasively programmed into the memory 994 through a telemetry circuit 1000 in telemetric communication with the external device 902, such as a programmer, transtelephonic transceiver or a diagnostic system analyzer, or with a bedside monitor. The telemetry circuit 1000 is activated by the microcontroller 960 by a control signal 1060. The telemetry circuit 1000 allows intra-cardiac electrograms, pressure data, acoustic data, SvO2 data, status information, and the like, as described above relating to the operation of IMD 910 (as contained in the microcontroller 960 or memory 994) to be sent to the external device 902 through an established communication link 1040.

The IMD 910 may also include an accelerometer or other physiologic sensor 1080, commonly referred to as a "rate-responsive" sensor because it is typically used to adjust pacing stimulation rate according to the exercise state of the patient. Optionally, the physiological sensor 1080 may further be used to detect changes in cardiac output, changes in the physiological condition of the heart, or changes in activity (e.g., detecting sleep and wake states) and to detect arousal from sleep. While shown as being included within IMD 910, it is to be understood that the physiologic sensor 1080 may also be external to IMD 910, yet still be implanted within or carried by the patient. A common type of rate responsive sensor is an activity sensor incorporating an accelerometer or a piezoelectric crystal, which is mounted within the housing 938 of IMD 910. The physiologic sensor 1080 may be used in conjunction with, or in place of, the position detector 965, for example.

The IMD 910 also includes a battery 1100, which provides operating power to all of the circuits shown. The IMD 910 is shown as having impedance measuring circuit 1120 which is enabled by the microcontroller 960 via a control signal 1140. Herein, impedance is primarily detected for use in evaluating ventricular end diastolic volume (EDV) but is also used to track respiration cycles. Other uses for an impedance measuring circuit include, but are not limited to, lead impedance, surveillance during the acute and chronic phases for proper lead positioning or dislodgement, detecting operable electrodes and automatically switching to an operable pair if dislodgement occurs, measuring respiration or minute ventilation; measuring thoracic impedance for determining shock thresholds; detecting when the device has been implanted, measuring stroke volume, and detecting the opening of heart valves, etc. The impedance measuring circuit 1120 is advantageously coupled to the switch 974 so that impedance at any desired electrode may be obtained.

Referring to FIGS. 1-12, various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EEPROM memory, and non-volatile RAM (NVRAM) memory. The above memory types are exemplary only, and are thus not limiting as to the types of memory usable for storage of a computer program.

Certain block diagrams of embodiments of the present disclosure illustrate various blocks labeled "module." It is to be understood that the modules represent circuit modules that may be implemented as hardware with associated instructions (for example, software stored on a tangible and non-transitory computer readable storage medium, such as a computer hard drive, ROM, RAM, or the like) that perform the operations described herein. The hardware may include state machine circuitry hard wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A charging energy control system comprising:
   an implantable medical device (IMD) including a battery, wherein the IMD is configured to receive charging energy to recharge the battery during a charging energy acceptance period, and reject the charging energy during an actual charging energy rejection period; and
   an external charger configured to transmit the charging energy to the IMD in order to recharge the battery, wherein the external charger includes a charging controller configured to:
   i) determine the actual charging energy rejection period,
   ii) regulate the charging energy during a charging energy regulation period in which the charging controller predicts a predicted charging energy rejection period of the IMD based on the actual charging energy rejection period, and
   iii) cease or reduce transmission of the charging energy during a charging energy conservation period that is at least a portion of the predicted charging energy rejection period.

2. The charging energy control system of claim 1, wherein the charging controller comprises:
   an energy-rejection prediction module configured to predict the predicted charging energy rejection period of the IMD based on the actual charging energy rejection period; and
   a charging cycling module configured to cease or reduce the transmission of the charging energy during the charging energy conservation period.

3. The charging energy control system of claim 1, wherein the charging energy conservation period equals the predicted charging energy rejection period.

4. The charging energy control system of claim 1, wherein the charging energy conservation period is a portion of the predicted charging energy rejection period.

5. The charging energy control system of claim 1, wherein the charging energy regulation period is triggered by an end of a communication session of the IMD.

6. The charging energy control system of claim 1, wherein the charging controller iteratively predicts subsequent predicted charging energy rejection periods and ceases or reduces transmission of the charging energy during subsequent charging energy conservation periods based on subsequent actual charging energy rejection periods until the IMD experiences or expects an interfering event.

7. The charging energy control system of claim 6, wherein the interfering event includes a communication session.

8. The charging energy control system of claim 1, wherein the IMD is one of an implantable pacemaker, an implantable cardioverter-defibrillator, a defibrillator, a cardiac rhythm management device, a neurostimulator, or an electrophysiology mapping and radio frequency ablation system.

9. The charging energy control system of claim 1, wherein the charging energy conservation period reduces a possibility of excess heating of one or both of the IMD and the external charger.

10. The charging energy control system of claim 1, wherein the charging energy conservation period does not overlap with any portion of the charging energy acceptance period.

11. A charging energy control method comprising:
    transmitting charging energy from an external charger to an implantable medical device (IMD);
    receiving the charging energy from the external charger at the IMD, wherein the receiving operation includes recharging a battery of the IMD with the received charging energy during a charging energy acceptance period, and rejecting the charging energy during an actual charging energy rejection period;
    regulating the charging energy during a charging energy regulation period with a charging controller, wherein the regulating operation includes:
        determining the actual charging energy rejection period;
        predicting a predicted charging energy rejection period of the IMD based on the actual recharging energy rejection period, and
        ceasing or reducing transmission of the charging energy during a charging energy conservation period that is at least a portion of the predicted charging energy rejection period.

12. The charging energy control method of claim 11, wherein the charging energy conservation period equals the predicted charging energy rejection period.

13. The charging energy control method of claim 11, wherein the charging energy conservation period is a portion of the predicted charging energy rejection period.

14. The charging energy control method of claim 11, further comprising triggering the charging energy regulation period with an end of a communication session of the IMD.

15. The charging energy control method of claim 11, wherein the regulating operation further comprises:
    iteratively predicting subsequent predicted charging energy rejection periods; and
    ceasing or reducing transmission of the charging energy during subsequent charging energy conservation periods based on subsequent actual charging energy rejection periods until the IMD experiences or expects an interfering event.

16. The charging energy control method of claim 11, wherein the IMD is one of an implantable pacemaker, an implantable cardioverter-defibrillator, a defibrillator, a cardiac rhythm management device, a neurostimulator, or an electrophysiology mapping and radio frequency ablation system.

17. The charging energy control method of claim 11, further comprising reducing a possibility of excess heating of one or both of the IMD and the external charger due to the regulating operation.

18. An external charger configured to recharge a battery of an implantable medical device (IMD), wherein the IMD is configured to receive charging energy from the external charger to recharge the battery during a charging energy acceptance period and reject the charging energy during an actual charging energy rejection period, the external charger comprising:
    a charging controller configured to:
        i) determine the actual charging energy rejection period,
        ii) regulate the charging energy during a charging energy regulation period in which the charging controller predicts a predicted charging energy rejection period of the IMD based on the actual recharging energy rejection period, and
        iii) cease or reduce transmission of the charging energy during a charging energy conservation period that is at least a portion of the predicted charging energy rejection period.

19. The external charger of claim 18, wherein the charging controller comprises:
    an energy-rejection prediction module configured to predict the predicted charging energy rejection period of the IMD based on the actual recharging energy rejection period; and
    a charging cycling module configured to cease or reduce the transmission of the charging energy during the charging energy conservation period.

20. The external charger of claim 18, wherein the charging controller iteratively predicts subsequent predicted charging energy rejection periods and ceases or reduces transmission of the charging energy during subsequent charging energy conservation periods based on subsequent actual charging energy rejection periods until the IMD experiences or expects an interfering event.

* * * * *